United States Patent [19]
Fischer et al.

[11] Patent Number: 5,713,945
[45] Date of Patent: Feb. 3, 1998

[54] IMPLANTABLE LEAD MODIFIED TO REDUCE TISSUE INGROWTH

[75] Inventors: Frank M. Fischer, Atherton; M. Elizabeth Bush, Fremont, both of Calif.

[73] Assignee: Pacesetter, Inc., Sunnyvale, Calif.

[21] Appl. No.: 664,045

[22] Filed: Jun. 13, 1996

[51] Int. Cl.$^6$ ..................................................... A61N 1/05
[52] U.S. Cl. .............................................. 607/122; 607/121
[58] Field of Search ................................. 600/1, 2; 607/122, 607/123, 120, 121; 128/641, 642, 659

[56] References Cited

U.S. PATENT DOCUMENTS

| | | | |
|---|---|---|---|
| 3,835,864 | 9/1974 | Rasor et al. | 128/419 |
| 3,902,501 | 9/1975 | Citron et al. | 128/418 |
| 5,059,166 | 10/1991 | Fischell et al. | 600/3 |
| 5,106,360 | 4/1992 | Ishiwara et al. | 600/2 |
| 5,176,617 | 1/1993 | Fischell et al. | 600/3 |
| 5,176,907 | 1/1993 | Leong | 424/78.08 |
| 5,411,550 | 5/1995 | Herweck et al. | 623/1 |
| 5,439,485 | 8/1995 | Mar et al. | 607/119 |

OTHER PUBLICATIONS

"Isostent Radioisotope Stent Expanded Scope of Use by Physicians", *MDDI Reports —The Gray Sheet*, Jul. 22, 1996, pp. I&W–9.

"Less–Invasive Techniques may Dominate Cardiovascular Therapy", *Cardiovascular Device Update*, Apr. 1996, pp. 1–16.

*Primary Examiner*—Scott M. Getzow
*Attorney, Agent, or Firm*—Steven M. Mitchell; M. Elizabeth Bush

[57] ABSTRACT

An implantable lead for use with an implantable pacemaker/cardioverter/defibrillator. Since irradiation from a radioisotope source is capable of inhibiting the growth of hyperproliferating cells as compared with normal cells, a radioisotope material which is incorporated into the lead can be used to decrease the rate of fibrotic growth. The radioisotope may be located inside the lead, alloyed into the metal from which the lead electrode or conductor is made, molded into rubber portions of the lead, or coated onto the conductor or electrode's surface. Beta emitting radioisotopes would be best suited as a radioactive material because of their comparatively short range of action within human tissue.

21 Claims, 4 Drawing Sheets

IMPLANTABLE LEAD MODIFIED TO REDUCE TISSUE INGROWTH

FIELD OF THE INVENTION

The present invention relates generally to body implantable electrical leads, and more specifically to an implantable lead modified with a radioactive isotope to inhibit fibrotic tissue growth.

BACKGROUND OF THE INVENTION

The use of implantable electrical leads to diagnose or treat cardiac arrhythmias is well accepted. Implanted pacing and defibrillation are normally accomplished by passing a current between at least a pair of implanted electrodes. Electrical current is supplied to the electrodes by a battery powered pulse generator implanted under the skin of the patient, either in the abdominal or pectoral region. The electrode arrangement may include a combination of intravenous, endocardial, epicardial, and/or subcutaneous leads. For example, bipolar pacing and sensing are generally accomplished using two closely-spaced electrodes positioned transvenously within the atrium or ventricle or on the epicardium. Unipolar pacing is typically between an endocardial electrode (atrial or ventricular) and the pacemaker pulse generator housing. For implantable cardioverter defibrillators (ICD), a typical lead system may include one large surface area right ventricular (RV) endocardial defibrillation electrode, and a second electrode positioned subcutaneously, such as a pulse generator housing electrode or patch electrode. A defibrillation electrode may be positioned transvenously within the superior vena cava (SVC), either in place of or in addition to the subcutaneous electrode. Various other electrode combinations are common for both pacing and defibrillation.

A technique for fixation of transvenous endocardial leads within the heart of a patient is described in U.S. Pat. No. 3,902,501 to Citron et al. which uses a plurality of pliant fixation tines which extend at an acute angle to the lead body from the distal tip of the lead. When the lead is extended into the right ventricle, the tines act as an anchor catching in the trabeculae of the heart wall. Over time, the growth of tissue around the tines will further act to secure the lead tip in place. A recurrent problem is excessive fibrotic tissue growth at the site of the pacing electrode or along the lead body.

Maintenance of stable and low acute and chronic pacing stimulation thresholds is highly desirable. Fibrous tissue is insensitive to stimulation; the nearest viable tissue will be stimulated if its threshold is reached. Extensive fibrosis about an electrode increases the size of the "virtual" electrode, which is the surface area of the encasement of such tissue about an electrode. Because threshold is directly related to "virtual" electrode size due to decreasing current density with increasing size, the larger the fibrotic area, the higher the threshold. This increase in pacing threshold necessitates an increase in generator output in order to stimulate the heart, which in turn decreases battery life. In some cases, the maximum output of the pulse generator is insufficient to counteract the decrease in current density due to the inactive tissue surrounding the electrode, leaving the patient with no way to artificially pace the heart.

Another undesired effect of a "virtual" electrode produced by a fibrous tissue layer is reduction of the electrogram amplitude, which can be especially important in the case of atrial sensing electrodes.

In some instances, lead removal may be necessitated by infection, fatigue failures, insulation abrasion, or other problems. Excessive fibrotic growth into electrodes and fixation mechanisms, and adhesions along the lead body to the tricuspid valve or insertion vein, results in a lead that is very difficult to extract. Various techniques for extracting adherent leads have been devised, including slow traction (hanging progressively heavier weights on the lead and waiting) and locking guidewire techniques through the venous implant site or a femoral route using specially-designed hardware. In some cases the adhesions are so extensive that the lead may need to be removed by open heart surgery.

It is therefore an object of the invention to provide an implantable electrical lead which inhibits fibrotic tissue ingrowth into the lead.

SUMMARY OF THE INVENTION

The present invention uses a radioisotope in an implantable lead which can irradiate the tissue in close proximity to the implantation site of the lead to reduce the rapid tissue growth caused by trauma to the endocardium, tricuspid valve, and vein from an indwelling lead. The invention is based on the knowledge that radiation therapy can reduce the proliferation of rapidly growing cancer cells in a malignant tumor. By incorporating a radioactive material having a relatively short half-life into a selected portion of the lead, fibrotic growth can be inhibited in the region surrounding that selected lead portion, while still allowing a certain amount of fibrosis for tip stabilization or other desired attachment points.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
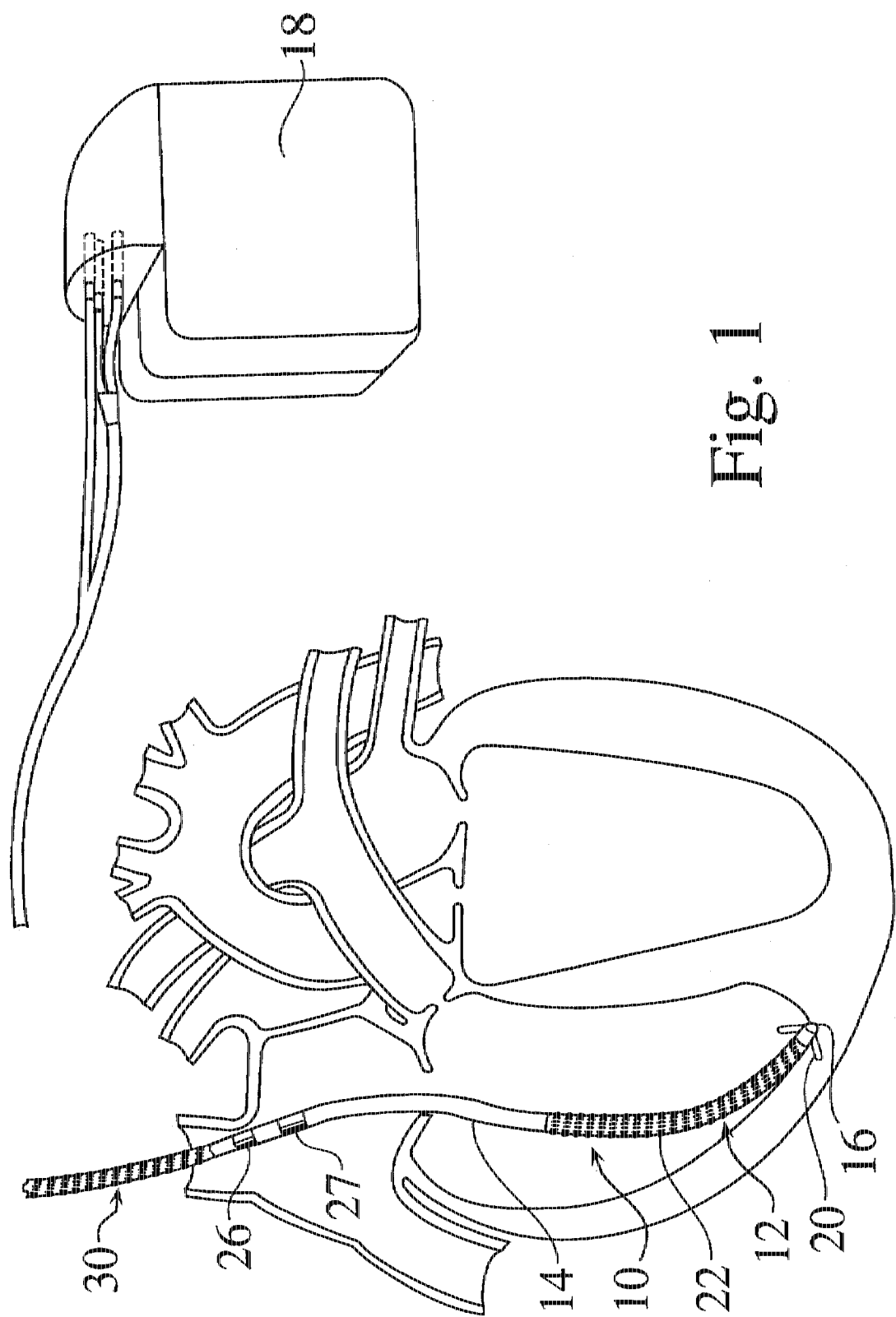
FIG. 1 shows a lead of the invention implanted in a human heart shown in partial section.

An endocardial lead according to the invention will now be described with reference to FIGS. 1–7. An endocardial lead 10 shown in FIG. 1 includes a defibrillation/sensing electrode 12 proximal of the distal end of lead 10 and extending along the lead body 14, and a pacing/sensing electrode 16 at the distal tip of lead 10. The proximal end of lead is connected to an ICD 18 of known construction. Lead 10 may include tines 20 to aid in fixation of the distal end within the apex of the patient's heart. Alternatively, a helical screw may be provided as a fixation device.

Defibrillation/sensing electrode 12 is in the form of a conductive electrode coil 22 wound around the periphery of lead body 14. Electrode coil 22 may be of the type disclosed in U.S. Pat. No. 5,439,485 entitled Flexible Defibrillation Electrode of Improved Construction, which is assigned to the assignee of the present application and is incorporated herein by reference. Other known electrode configurations may also be used. Electrode coil 22 is connected to a lead conductor 24 (see FIG. 6) at at least one point, preferably its distal end. Also included on lead 10 are two atrial electrodes 26, 27 which may be used for sensing and/or pacing and are located approximately 14 centimeters from the distal end of lead 10.

Defibrillation electrode 12 of lead 10 may be used in conjunction with a subcutaneous (SQ) electrode such as the housing of ICD 18 or a flexible patch. In addition to or instead of the SQ electrode, an SVC electrode 30 may be used, and may be located on lead 10 or may be on a separate lead.

Figure 2:
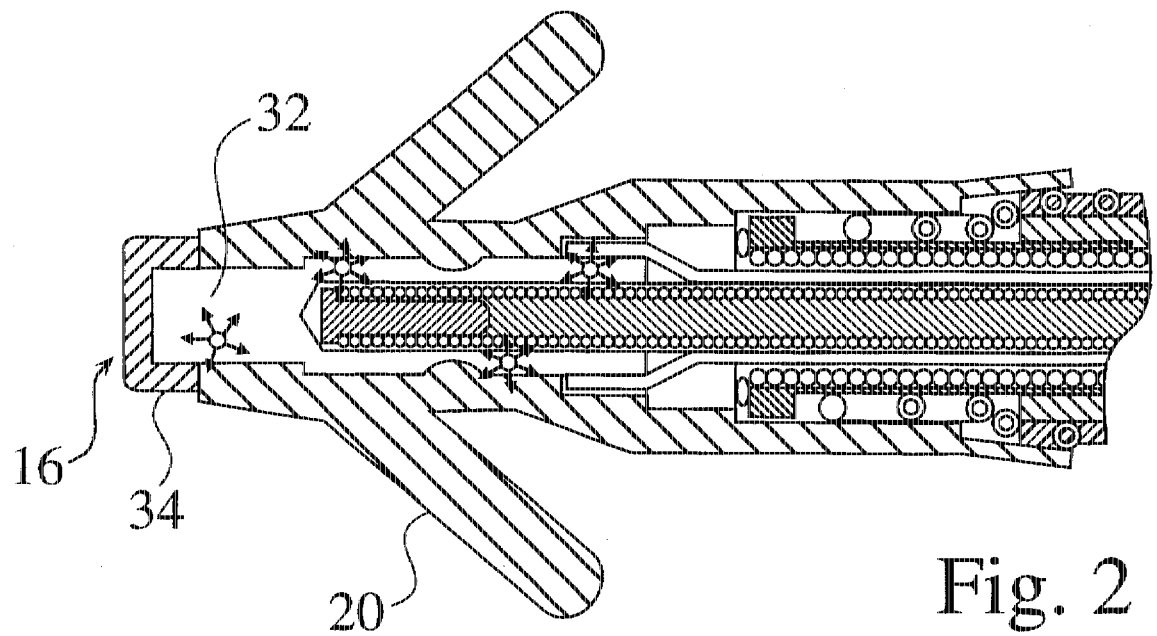
FIG. 2 is a cross section through the electrode showing a radioisotope core material within an electrode shank.

FIG. 2 shows pacing electrode 16 in cross section in which shank 32 is made from a radioactive material. The stimulating tip 34 which is exposed to the body, is made of a biocompatible, inert material, such as platinum iridium, activated carbon or TiN. Radioactive shank 32 is completely encapsulated by silicone rubber tines 20, which may be insert molded directly onto electrode shank 32 or may be molded as a separate piece, then bonded on with silicone adhesive.

Electrode shank 32 may be fabricated from a pure metal or alloy which has been irradiated so that it has become radioactive; i.e., it is a radioisotope. The arrows pointing outward from the cross section indicate the omnidirectional emission of particles from electrode shank 32. The purpose of this radiation is to decrease the rate of proliferative cell growth of the traumatized endocardium or venous wall. Thus it would be expected that stimulation thresholds will not increase appreciably, electrogram amplitudes will not decrease appreciably, and the lead will remain explantable if necessary without having to resort to extraordinary means.

The radioisotope used for this purpose may be an alpha, beta or gamma emitter. The half-life would ideally be between 10 hours and 100 days. An optimum emitter might be a beta emitting isotope such a vanadium which has a half-life of 16 days and only 8% of its emitted energy is from gamma radiation. The ideal attribute of a beta emitter is that the radiation does not travel very far in human tissue. Thus only the tissue in close proximity to the radioisotope lead will be affected. Furthermore only moderate levels of radiation are desired since it is known that very high levels can cause injury to nonproliferating tissues.

Shank 32 may alternatively be made from a metal into which is alloyed an element that can be made into a radioisotope. For example, phosphorus, a 14.3 day half-life beta emitter, could be alloyed into steel which could be used for electrode shank 32.

One drawback of using a radioisotope with a short half-life is that manufacturing and storage of the lead would pose some logistical problems. From the time the lead is manufactured, either using a radioisotope directly or irradiating material to form a radioisotope, to the time the lead is implanted in the patient, a certain amount of radioisotope will have decayed. Any delay in shipping, or time spent on the shelf of a hospital supply room or company stock room would decrease the amount of radioisotope available in the lead for therapeutic use. These logistical problems would be lessened by using a radioisotope with a half-life longer than 100 days.

Figure 3:
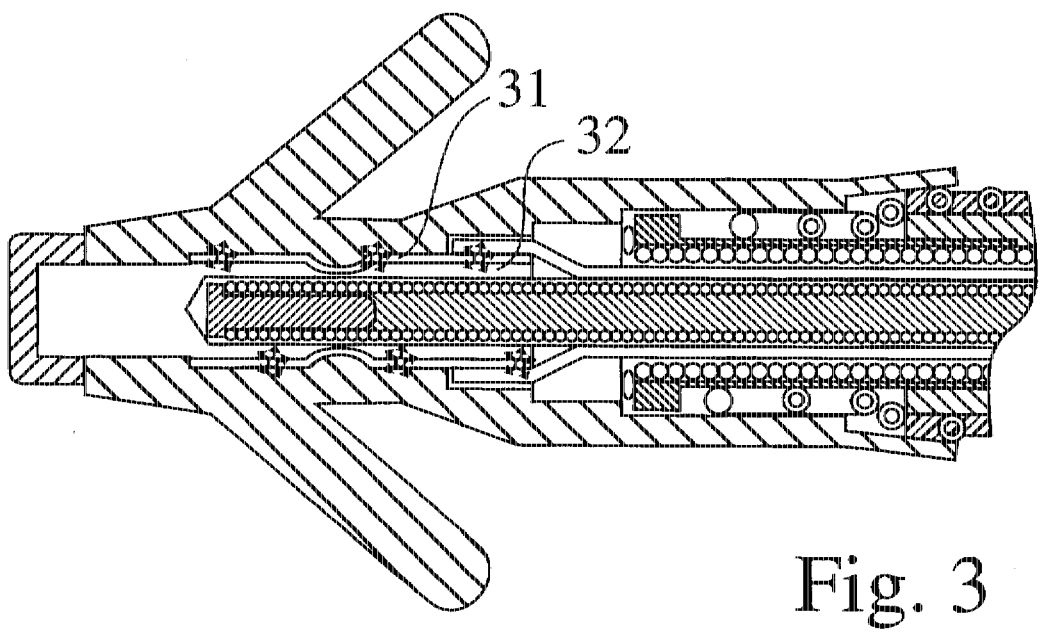
FIG. 3 is a cross section through the electrode showing a thin plating of radioisotope material on the surface the electrode shank.

FIG. 3 shows a cross section of an alternative embodiment of the present invention in which a radioisotope coating 31 is plated onto electrode shank 32. For example, the beta emitting isotope gold 198 (half-life 2.7 days) could be used to coat any suitable metal.

Figure 4:
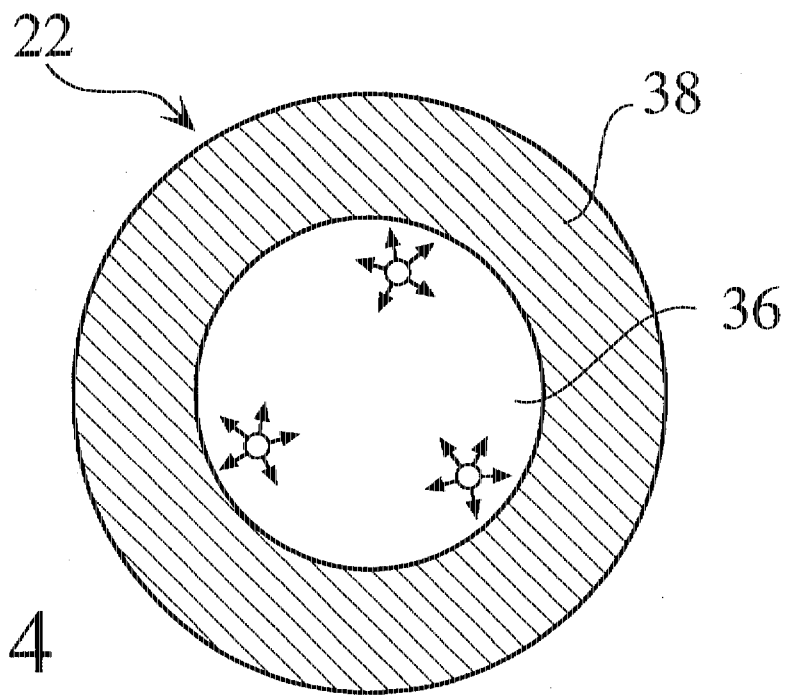
FIG. 4 is a conductor wire cross section.

A radioactive material may be used at locations within the lead structure other than or in addition to the pacing electrode shank so as to attenuate tissue growth in desired areas. For example, FIG. 4 is a cross section of a wire made from a radioisotope core 36, such as Au 198, within an outer covering 38, such as PtIr, that has the attributes that are desirable for being an electrode coil 22. This structure may be made by the drawn filled tube (DFT) process of Fort Wayne Metals (Fort Wayne, Ind.) or by plating or depositing outer covering 38 onto radioisotope core 36. This structure may also be used for conductor coil 24.

Figure 5:
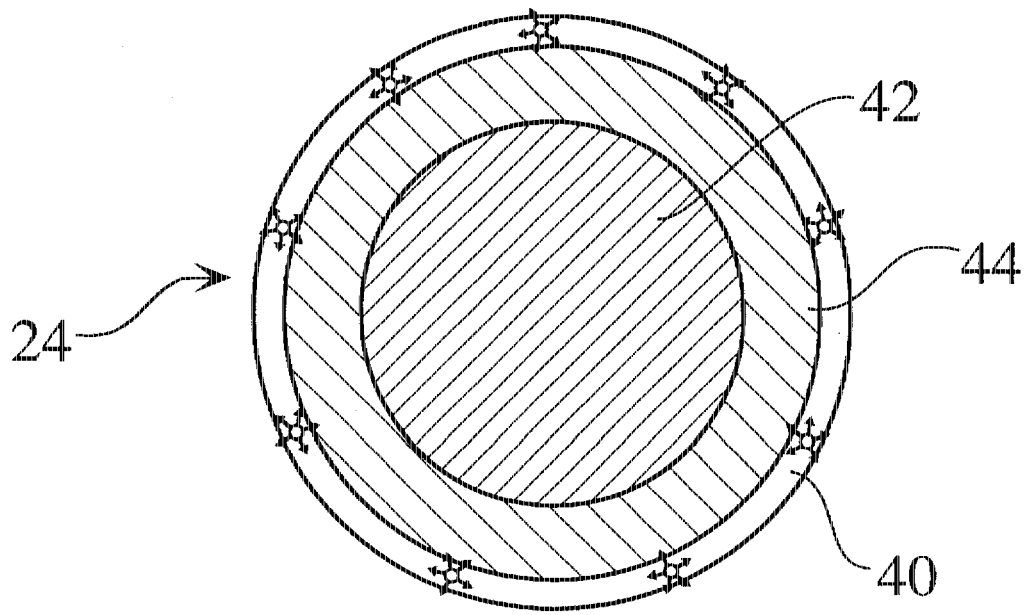
FIG. 5 is a cross section of conductor coil plated with a radioisotope.

FIG. 5 is a cross section of an alternative embodiment of the present invention in which a radioisotope jacket 40, such as the beta emitting isotope gold 198, forms the outer layer of conductor coil 24. The structure shown is DFT having a silver core 42 with a tube of MP35N 44 drawn over it. Radioisotope jacket 40 may also be formed as a drawn tube, or may be plated onto the Ag/MP35N DFT structure. The conductor coil 24 is covered by a biocompatible material (not shown), which may be silicone rubber, a fluoropolymer such as polytetrafluoroethylene (PTFE), or polyurethane. The wire structure of FIG. 5 may also be used to form electrode coil 22.

Figure 6:
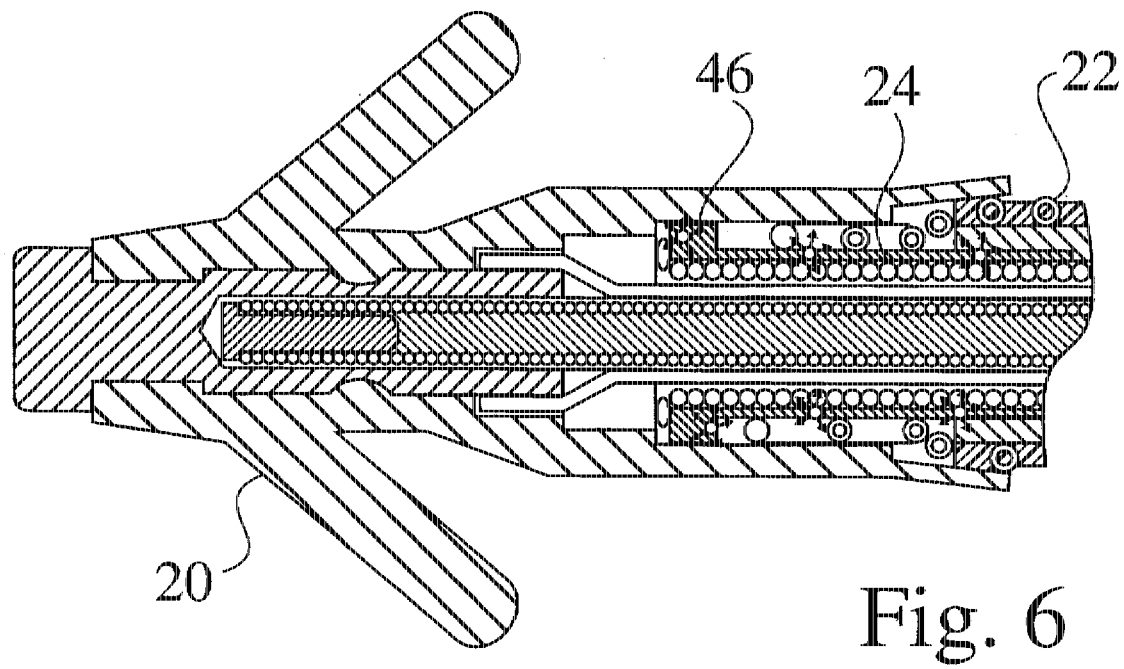
FIG. 6 is a cross section of a joining sleeve plated with a radioisotope.

FIG. 6 is a cross section of the joint formed between the defibrillation electrode and the conductor coil. The joint includes a sleeve 46 to which both conductor coil 24 and electrode coils 22 have been welded. Alternatively, the coils may be crimped to sleeve 46. Sleeve 46 is plated with a radioisotope. Alternatively, sleeve 46 may be made from a metal into which is alloyed an element that can be made into a radioisotope.

Figure 7:
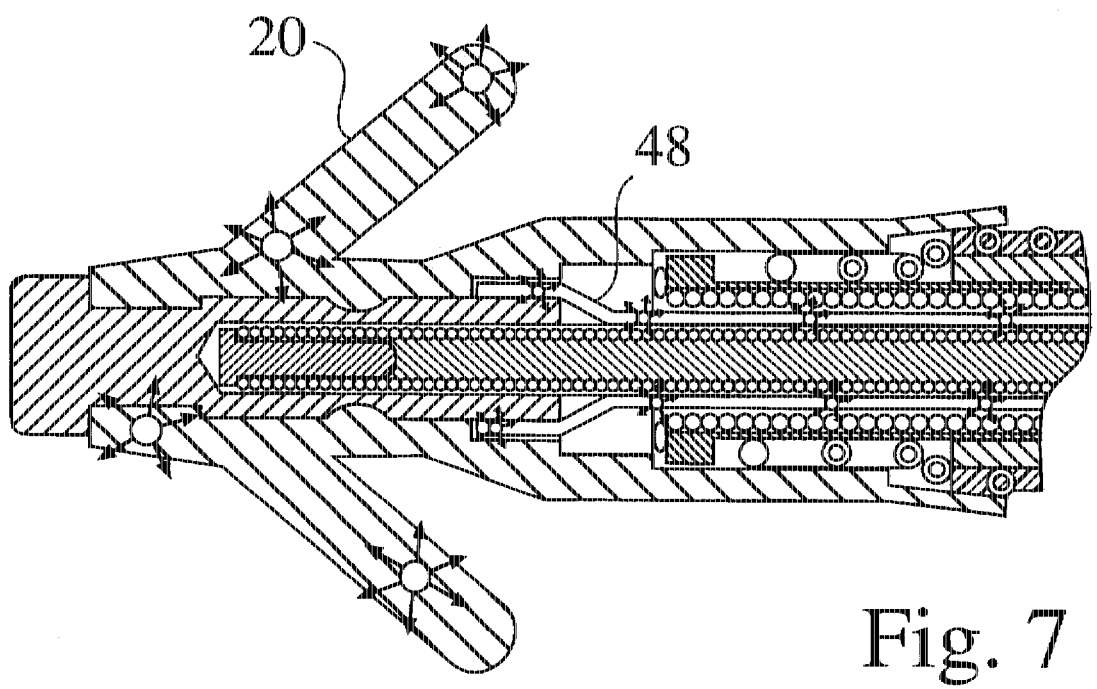
FIG. 7 is a cross section of radioactive tines and tubing.

FIG. 7 is a cross section of the distal end of lead 10 showing tines 20 having a small amount of radioactive material molded into them. In addition, insulating tubing 48 also has a small amount of radioactive material molded into it.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. An implantable lead comprising:
   a lead body having a distal end for positioning within a patient's body and a proximal end having a connector for connection to an implantable pulse generator;
   an electrode positioned on said lead body and electrically coupled to said connector via a conductor; and
   a radioactive material located on a portion of said lead body so that said radioactive material emits radiation that can reduce the proliferation of cells that are in close proximity to said lead body portion, wherein said electrode comprises structural material and wherein said radioactive material is located within said structural material.

2. The implantable lead of claim 1 in which the radioactive material emitting the radiation is a radioisotope.

3. The implantable lead of claim 2 wherein said radioisotope is a beta particle emitting radioisotope.

4. The implantable lead of claim 2 wherein said radioisotope has a half-life of less than 100 days.

5. The implantable lead of claim 2 wherein said radioisotope has a half-life of greater than 100 days.

6. The implantable lead of claim 1 wherein said electrode is a tip electrode.

7. The implantable lead of claim 1 wherein said electrode is a defibrillation electrode.

8. An implantable lead comprising:

a lead body having a distal end for positioning within a patient's body and a proximal end having a connector for connection to an implantable pulse generator;

an electrode positioned on said lead body and electrically coupled to said connector via a conductor; and a radioactive material located on a portion of said lead body so that said radioactive material emits radiation that can reduce the proliferation of cells that are in close proximity to said lead body portion, wherein said radioactive material is plated onto at least a portion of said electrode.

9. The implantable lead of claim 8 wherein said electrode is a tip electrode.

10. The implantable lead of claim 8 wherein said electrode is a defibrillation electrode.

11. An implantable lead comprising:

a lead body having a distal end for positioning within a patient's body and a proximal end having a connector for connection to an implantable pulse generator;

an electrode positioned on said lead body and electrically coupled to said connector via a conductor; and a radioactive material located on a portion of said lead body so that said radioactive material emits radiation that can reduce the proliferation of cells that are in close proximity to said lead body portion, wherein said conductor comprises structural material and wherein said radioactive material is located within said structural material of said conductor.

12. An implantable lead comprising:

a lead body having a distal end for positioning within a patient's body and a proximal end having a connector for connection to an implantable pulse generator;

an electrode positioned on said lead body and electrically coupled to said connector via a conductor; and a radioactive material located on a portion of said lead body so that said radioactive material emits radiation that can reduce the proliferation of cells that are in close proximity to said lead body portion, wherein said radioactive material is plated onto at least a portion of said conductor.

13. An implantable lead comprising:

a lead body having a distal end for positioning within a patient's body and a proximal end having a connector for connection to an implantable pulse generator;

an electrode positioned on said lead body and electrically coupled to said connector via a conductor;

a radioactive material located on a portion of said lead body so that said radioactive material emits radiation that can reduce the proliferation of cells that are in close proximity to said lead body portion; and a joining piece coupling said electrode to said conductor, wherein said radioactive material is located within said joining piece.

14. An implantable lead comprising:

a lead body having a distal end for positioning within a patient's body and a proximal end having a connector for connection to an implantable pulse generator;

an electrode positioned on said lead body and electrically coupled to said connector via a conductor;

a radioactive material located on a portion of said lead body so that said radioactive material emits radiation that can reduce the proliferation of cells that are in close proximity to said lead body portion; and a joining piece coupling said electrode to said conductor, wherein said radioactive material is plated onto said joining piece.

15. An implantable lead comprising:

a lead body having a distal end for positioning within a patient's body and a proximal end having a connector for connection to an implantable pulse generator;

an electrode positioned on said lead body and electrically coupled to said connector via a conductor;

a radioactive material located on a portion of said lead body so that said radioactive material emits radiation that can reduce the proliferation of cells that are in close proximity to said lead body portion; and a plurality of tines located at said distal end, wherein said radioactive material is located within said tines.

16. An implantable lead comprising:

a lead body having a distal end for positioning within a patient's body and a proximal end having a connector for connection to an implantable pulse generator;

an electrode positioned on said lead body and electrically coupled to said connector via a conductor; and a radioactive material located on a portion of said lead body so that said radioactive material emits radiation that can reduce the proliferation of cells that are in close proximity to said lead body portion, wherein said lead body further comprises insulated tubing, and wherein said radioactive material is extruded into said insulated tubing.

17. An implantable lead comprising:

a lead body having a distal end for positioning within a patient's body and a proximal end having a connector for connection to an implantable pulse generator;

an electrode positioned on said lead body and electrically coupled to said connector via a conductor; and a radioactive material located on a portion of said lead body so that said radioactive material emits radiation that can reduce the proliferation of cells that are in close proximity to said lead body portion, wherein said radioactive material is covered by a biocompatible metal.

18. An implantable lead comprising:

a lead body having a distal end for positioning within a patient's body and a proximal end having a connector for connection to an implantable pulse generator;

an electrode positioned on said lead body and electrically coupled to said connector via a conductor; and a radioactive material located on a plurality of portions of said lead body so that said radioactive material emits radiation that can reduce the proliferation of cells that are in close proximity to said lead body portion.

19. An implantable lead comprising:

a lead body having a distal end for positioning within a patient's body and a proximal end having a connector for connection to an implantable pulse generator;

a cardiac pacing electrode positioned on said lead body and electrically coupled to said connector via a conductor; and a radioactive material located on a portion of said lead body so that said radioactive material emits radiation that can reduce ingrowth of tissue into said lead.

20. An implantable system comprising:
   a lead comprising:
      a lead body having a distal end for positioning within a patient's body and a proximal end having a connector;
      an electrode positioned on said lead body and electrically coupled to said connector via a conductor; and
      a radioactive material located on a portion of said lead body so that said radioactive material emits radiation that can reduce ingrowth of tissue into said lead; and
   an implantable pulse generator electrically coupled to said lead via said connector.

21. An implantable lead comprising:
   a lead body having a distal end for positioning within a patient's body and a proximal end having a connector for connection to an implantable pulse generator;
   a cardiac defibrillation electrode positioned on said lead body and electrically coupled to said connector via a conductor; and
   a radioactive material located on a portion of said lead body so that said radioactive material emits radiation that can reduce ingrowth of tissue into said lead.

* * * * *